(12) United States Patent
Tighe et al.

(10) Patent No.: US 9,492,175 B2
(45) Date of Patent: Nov. 15, 2016

(54) APPARATUSES AND METHODS FOR SUPPORTING AN UMBILICUS

(75) Inventors: Patrick James Tighe, Gainesville, FL (US); Nicole Dobija, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 485 days.

(21) Appl. No.: 13/383,317

(22) PCT Filed: Jul. 28, 2010

(86) PCT No.: PCT/US2010/043564
§ 371 (c)(1),
(2), (4) Date: Jan. 10, 2012

(87) PCT Pub. No.: WO2011/014566
PCT Pub. Date: Feb. 3, 2011

(65) Prior Publication Data
US 2012/0116174 A1    May 10, 2012

Related U.S. Application Data

(60) Provisional application No. 61/229,357, filed on Jul. 29, 2009.

(51) Int. Cl.
*A61B 17/122* (2006.01)
*A61M 25/02* (2006.01)
(Continued)

(52) U.S. Cl.
CPC ............. *A61B 17/122* (2013.01); *A61B 90/50* (2016.02); *A61M 25/02* (2013.01); *A61B 1/32* (2013.01);
(Continued)

(58) Field of Classification Search
CPC .................. A61B 17/122; A61B 19/26; A61B 17/02; A61B 17/0206; A61B 1/32;
(Continued)

(56) References Cited

U.S. PATENT DOCUMENTS 4,338,943 A   7/1982   Okamoto
4,470,410 A   9/1984   Elliott
(Continued)

FOREIGN PATENT DOCUMENTS

WO          8101519 A1    6/1981
WO       2007104866 A1    9/2007

OTHER PUBLICATIONS

The International Search Report and Written Opinion dated Apr. 26, 2011.

(Continued)

*Primary Examiner* — Ophelia A Hawthorne
*Assistant Examiner* — Keri J Nelson
(74) *Attorney, Agent, or Firm* — Thomas Horstemeyer, LLP

(57) ABSTRACT

In one embodiment, an umbilicus support apparatus includes a base and an armature that extends from the base, the armature including a flexible arm having a proximal end and a distal end, the armature further including a support head attached to the distal end of the arm, the support head including umbilicus securing means for securing an umbilicus.

20 Claims, 5 Drawing Sheets

(51) Int. Cl.
  *A61B 17/02* (2006.01)
  *A61B 1/32* (2006.01)
  *A61G 13/10* (2006.01)
(52) U.S. Cl.
  CPC ............ *A61B 17/0206* (2013.01); *A61B 90/30* (2016.02); *A61G 13/101* (2013.01); *A61M 2025/028* (2013.01); *A61M 2025/0213* (2013.01)
(58) Field of Classification Search
  CPC ............ A61B 17/0218; A61G 13/101; A61G 13/12; A61G 15/10
  USPC .......... 128/845; 606/120; 600/201, 215–219, 600/227–230, 235, 245
  See application file for complete search history.

(56) References Cited

U.S. PATENT DOCUMENTS

| | | | |
|---|---|---|---|
| 4,585,437 A | 4/1986 | Simms | |
| 4,781,188 A | 11/1988 | Collins | |
| 5,370,627 A | 12/1994 | Conway | |
| 5,395,344 A | 3/1995 | Beisang | |
| 5,415,633 A | 5/1995 | Lazarus | |
| 5,520,699 A | 5/1996 | Hessel | |
| 5,938,666 A | 8/1999 | Reynolds | |
| 5,984,945 A | 11/1999 | Sirhan | |
| 6,096,025 A | 8/2000 | Borders | |
| 6,688,306 B1 | 2/2004 | Cise | |
| 6,702,789 B1 | 3/2004 | Owens | |
| 6,729,326 B1 | 5/2004 | Winterton | |
| 6,780,195 B2 | 8/2004 | Porat | |
| 6,866,652 B2 | 3/2005 | Bierman | |
| 7,338,434 B1* | 3/2008 | Haarstad et al. | 600/37 |
| 7,395,563 B2* | 7/2008 | Whitmore, III | A61B 6/0442 248/276.1 |
| 8,078,261 B2 | 12/2011 | Imam | |
| 2006/0259018 A1* | 11/2006 | Shilkrut | 606/1 |
| 2007/0010005 A1 | 1/2007 | Sitzmann | |

OTHER PUBLICATIONS

Weber, Catheter Cadiovas.Interv. 2006, 67:947-55, Apr. 6, 2006.
Anderson, et al., "Umbilical Vascular Catheterization," The new England Journal of Medicine, 2008;359:e18.
Touijer, et al., "Laparascopic Radical Prostatectomy," Urologic Oncology, Seminars and Original Investigations 22 (2004, pp. 133-138.
Wilson, et al., "Central Venous Catheter Insertion in Neonates," Acta Pediatr Scand 79:855-860, 1990.
"Management of Peripheral Intravascular Devices," Best Practice, vol. 2, Issue 1, 1998, ISSN 1329-1874, pp. 1-6.
Ryder, Marcia. "Device Selection: A Critical Strategy in the Reduction of Catheter-Related Complications," Nutrition, vol. 12, No. 2, 1996, pp. 143-145.
O'Grady, et al., "Guidelines for the Prevention of Intravascular Catheter-Related Infections," Pediatrics, Official Journal of the American Academy of Pediatrics, 2002, pp. 1-24.
Pettit, Janet, "Fostering a New Era of Vascular Access Device Selection in Neonates," Newborn and Infant Nursing Reviews, vol. 6, No. 4 Dec. 2006, pp. 186-192.

* cited by examiner

APPARATUSES AND METHODS FOR SUPPORTING AN UMBILICUS

CROSS-REFERENCE TO RELATED APPLICATION

This application is the 35 U.S.C. §371 national stage of PCT application PCT/US2010/043564, filed Jul. 28, 2010, which claims priority to and the benefit of U.S. Provisional Application No. 61/229,357, filing date Jul. 29, 2009, which is hereby incorporated by reference in its entirety.

BACKGROUND

Peripheral blood vessels in neonates are often friable and difficult to access, particularly in the preterm population. Because of this, traditional central venous catheters can be difficult to place. For this reason, umbilical artery catheters (UACs) and umbilical vein catheters (UVCs) are used to provide access for various purposes, such as resuscitation, monitoring of blood, administration of fluids, blood transfusion, and parenteral nutrition in neonates whose condition is unstable.

Placement of umbilical catheters is important in the treatment of ill neonates. Under current practice, the umbilicus is normally elevated by an assistant and the umbilicus is sterilized and draped in preparation for cannulation. During cannulation, the assistant typically holds the umbilicus in an upright orientation with the neonate supine to enable the physician to perform the cannulation.

Although the above-described procedure is viable, it is disadvantageous because at least one assistant, who must be sufficiently sterilized prior to assisting, is required. More desirable would be a procedure that does not rely on the availability of such an assistant.

BRIEF DESCRIPTION OF THE DRAWINGS

The disclosed apparatuses and methods can be better understood with reference to the following drawings. The components in the drawings are not necessarily to scale.

DETAILED DESCRIPTION

As described above, it is current practice to have a sterilized assistant manually support the umbilicus both during preparation for and performance of umbilical vessel cannulation. Such a practice is disadvantageous because at least one assistant is required. Described herein are apparatuses and methods that remove the need for such an assistant. In one embodiment, an apparatus comprises an armature that supports the umbilicus in an upright (e.g., vertical) orientation.

Figure 1:
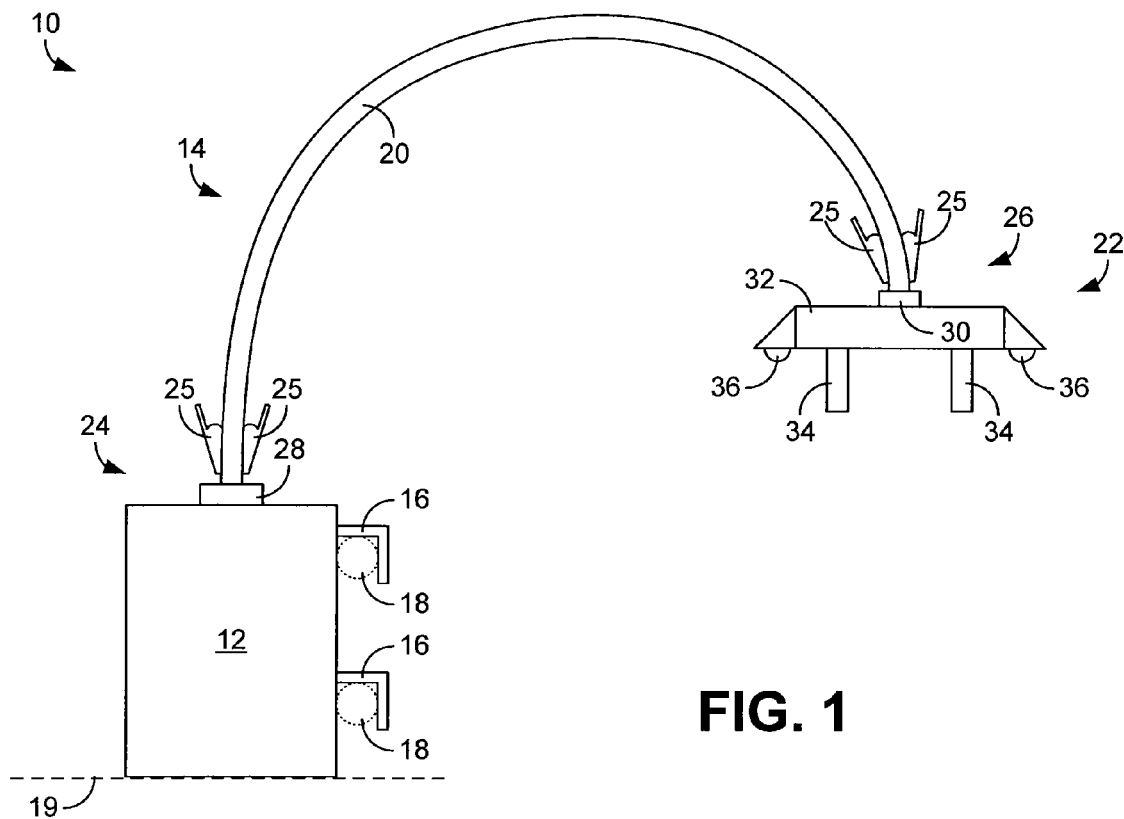
FIG. 1 is a schematic side view of an embodiment of an umbilicus support apparatus that can assist with umbilical vessel cannulation.

FIG. 1 illustrates an embodiment of an umbilicus support apparatus 10 designed to support an umbilicus, or umbilical cord, before, during, or after an umbilical vessel cannulation procedure. It will be appreciated, however, that the apparatus 10 can be used to support an umbilicus even when an umbilical vessel cannulation is not to be performed.

As indicated in FIG. 1, the apparatus 10 generally includes a base 12 and an armature 14 that extends out from the base. The base 12 is, for example, designed to secure to a bed on which the neonate lays or an incubator in which the neonate is placed. In some embodiments, the base 12 includes one or more clamp members 16 that extend from a side of the base that are designed to clamp onto rails 18 of the bed or incubator. Alternatively, the base 12 may be placed on a support surface 19 associated with or positioned near the bed or incubator, such as a side tray or platform. The base 12 can comprise various electrical components, such as a power switch, an internal power source (e.g., battery), and various electronics that control operation of the apparatus 10. Although the base 12 has been described as potentially including an internal power source, the base may alternatively use A/C current supplied by a wall outlet or other source.

The armature 14 includes an elongated flexible arm 20 and a support head 22. The arm 20 has a first or proximal end 24 and a second or distal end 26. As shown in FIG. 1, the arm 20 is connected to the base 12 at its proximal end 24 and the support head 22 is attached to the arm at its distal end 26. In the illustrated embodiment, the arm 20 extends from the top of the base 12. In some embodiments, the arm 20 can be rotated relative to the base 12 (about the longitudinal axis of the arm) to enable desired positioning of the support head 22. A lock collar 28 can be provided adjacent the base 12 and the proximal end 24 of the arm 20 to enable selective locking of the angular position of the arm relative to the base. Also positioned adjacent the proximal end 24 of the arm 20 are one or more clips 25 that are adapted to secure a sterile drape or sheath (not shown) that can extend from the proximal end to the distal end 26 of the arm. Further clips 25 can also be provided at the distal end 26 of the arm 20 for that purpose.

In addition to being angularly adjustable, the arm 20 can be flexed to change the position and/or orientation of the support head 22. In some embodiments, the arm 20 provides mild resistance against such flexion and is configured so that the arm will automatically hold substantially any position and/or orientation in which it is placed in similar manner to a flexible table lamp. In some embodiments, the arm 20 includes fixation elements (not shown) that are used to securely fix the arm in a desired position.

As noted above, the support head 22 is attached to the distal end 26 of the arm 20. In some embodiments, the support head 22 can be rotated relative to the arm 20. In such cases, the armature 14 can include a lock collar 30 that securely locks the support head in a desired angular orientation relative to the arm 20. In some embodiments, the support head 22 comprises an elongated body 32 that supports one or more umbilicus clamp securing elements 34 and, in at least some embodiments, one or more lights 36 that face downward from the head. The securing elements 34 are designed to hold an independent umbilicus clamp (see FIG. 2) as a means for supporting the umbilicus to which the clamp is attached. In some embodiments, the securing elements 34 comprise clips or clamps that are adapted to grip the ends of the umbilicus clamp. An example embodiment for the securing elements 34 is described below in relation to FIGS. 4 and 5. When provided, the lights 36 illuminate the umbilicus when secured by the apparatus 10 to aid the physician during umbilical vessel cannulation.

In some embodiments, the support head 22 is removable to facilitate the attachment of alternative support heads to the distal end 26 of the flexible arm 20. Such alternative support heads may comprise alternative configurations, dimensions, securing elements, and/or lights. In some embodiments, the umbilicus clamp securing elements 34 are separately removable and replaceable. For example, the securing elements 34 can be disposable elements that are discarded after use in supporting an umbilicus.

Figure 2:
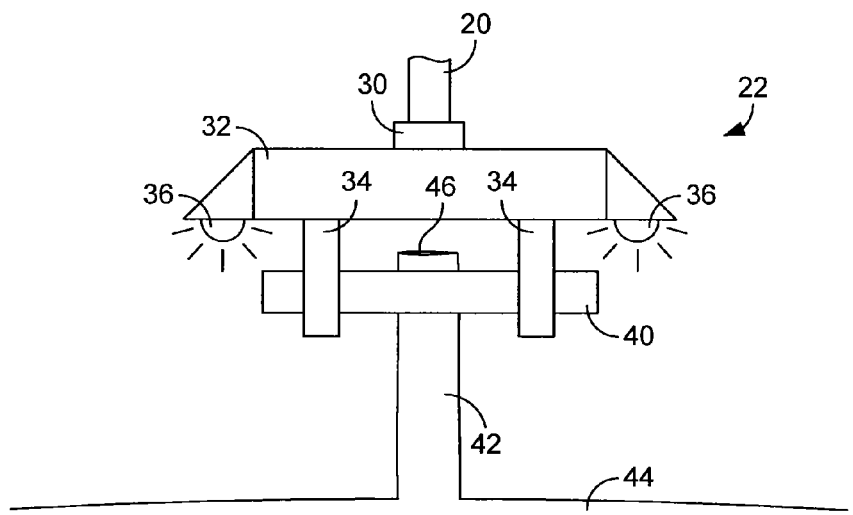
FIG. 2 is a partial schematic side view of the support apparatus of FIG. 1 shown in use supporting an umbilicus.

FIG. 2 illustrates an example of use of the umbilicus support apparatus 10 of FIG. 1. As shown in FIG. 2, an umbilicus clamp 40 that has been clamped around an umbilicus 42 of a neonate 44 has been secured by the umbilicus clamp securing elements 34 of the apparatus 10. In the illustrated example, such securing results in umbilicus 42 being supported in an upright (vertical) orientation and a distal tip 46 of the umbilicus being directed upward toward the support head 22. In that orientation, light emitted from the lights 36 can shine upon the umbilicus 42 to aid the physician in inserting a catheter in an appropriate umbilical vessel.

Figure 3:
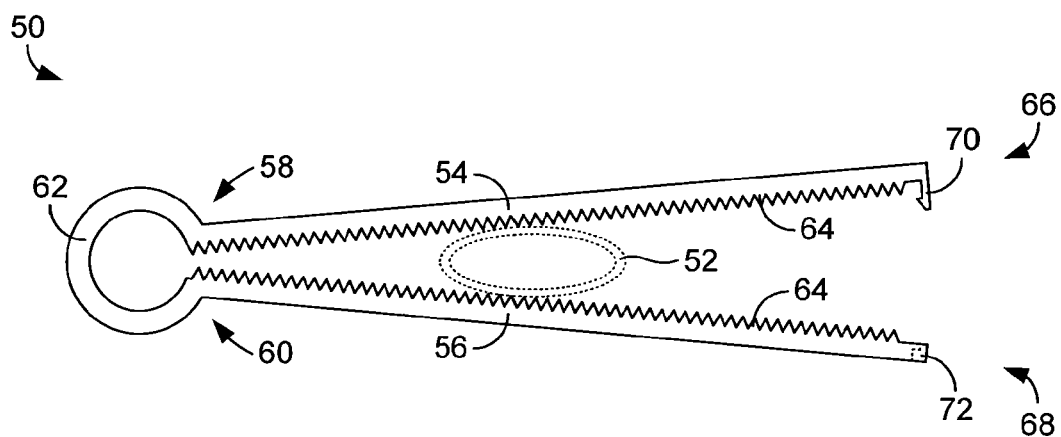
FIG. 3 is a top view of an example umbilicus clamp that can be secured by the apparatus of FIG. 1.

FIG. 3 depicts an example umbilicus, or umbilical cord, clamp 50 that can be used to close an umbilicus 52. As shown in FIG. 3, the clamp 50 generally comprises first and second opposed arms 54, 56 that are joined together at their first or proximal ends 58, 60 by a flexible hinge 62. Provided along inner sides of the arms 54, 56 are serrations or teeth 64 that ensure secure gripping of the umbilicus 52. Provided at the second or distal ends 66, 68 of the arms 54, 56 are locking elements. In the illustrated embodiment, the locking elements comprise a prong 70 provided at the distal end 66 of the first arm 54 that is adapted to be received by a complimentary recess 72 provided at the distal end 68 of the second arm 56 in a snap fitting arrangement. In use, the arms 54, 56 can be closed down on the umbilicus 52 until the prong 70 is received by the recess 72. Once the clamp 50 has been secured to the umbilicus 52 in that manner, the clamp (and therefore the umbilicus) can be supported in a desired orientation with the apparatus 10.

Figure 4:
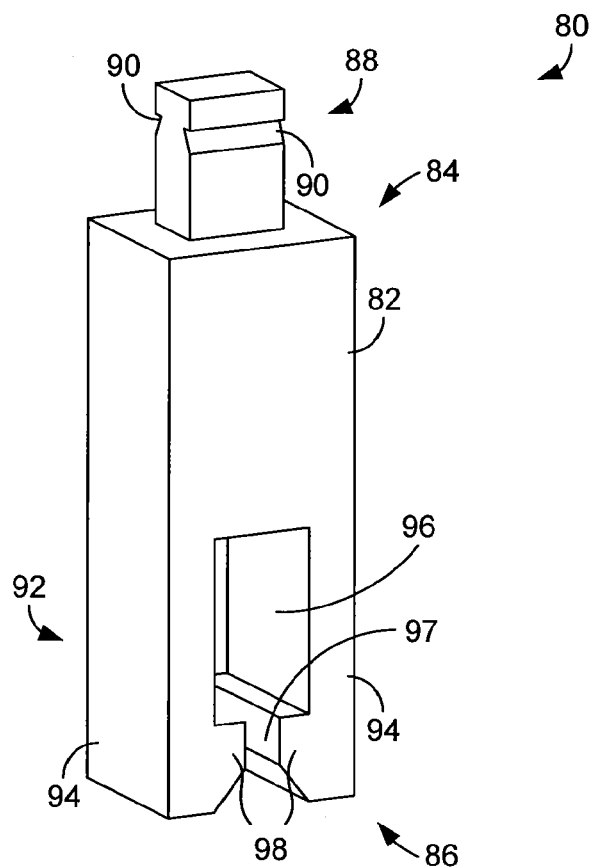
FIG. 4 is a perspective view of an embodiment of an umbilicus clamp securing element that can form part of the apparatus of FIG. 1.

FIG. 4 illustrates an example umbilicus clamp securing element 80 that can form part of the apparatus 10 of FIG. 1. As indicated in FIG. 4, the securing element 80 comprises a body 82. In the illustrated embodiment, the body 82 is a generally block-shaped solid member that includes a top end 84 and a bottom end 86. In some cases, the body can be unitarily constructed from a polymeric material. Extending upward from the top end 84 of the body 82 is a shank 88 that is adapted to be received by a complementary orifice of the support head 22 (not shown). The shank 88 is elongated and comprises one or more notches 90 that are adapted to receive complementary detents provided within the support head orifice (not shown).

Provided at the bottom end 86 of the body 82 is a clip element 92 that is specifically configured to receive and secure an umbilicus clamp, such as the clamp 50 shown in FIG. 3. In the illustrated embodiment, the clip element 92 comprises opposed flexible arms 94 that each defines part of an opening 96 in which the umbilicus clamp can be received. The opening 96 is partially closed by inwardly-extending prongs 98 that are provided at the distal ends of the arm 94.

Figure 5A:
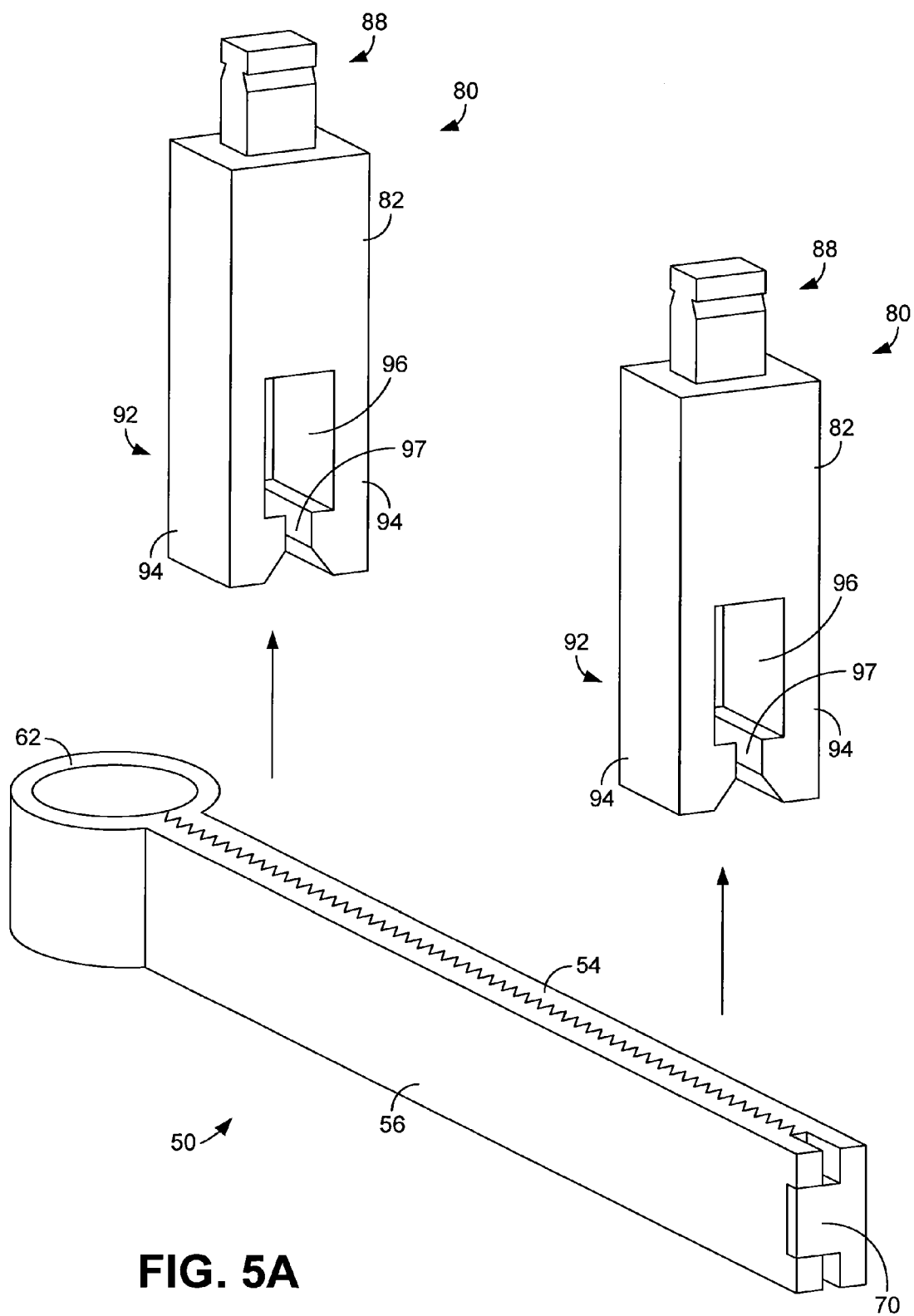
FIGS. 5A and 5B are schematic perspective views that illustrate the manner in which the umbilicus clamp of FIG. 3 can be secured by securing elements of the apparatus of FIG. 1.
Figure 5B:
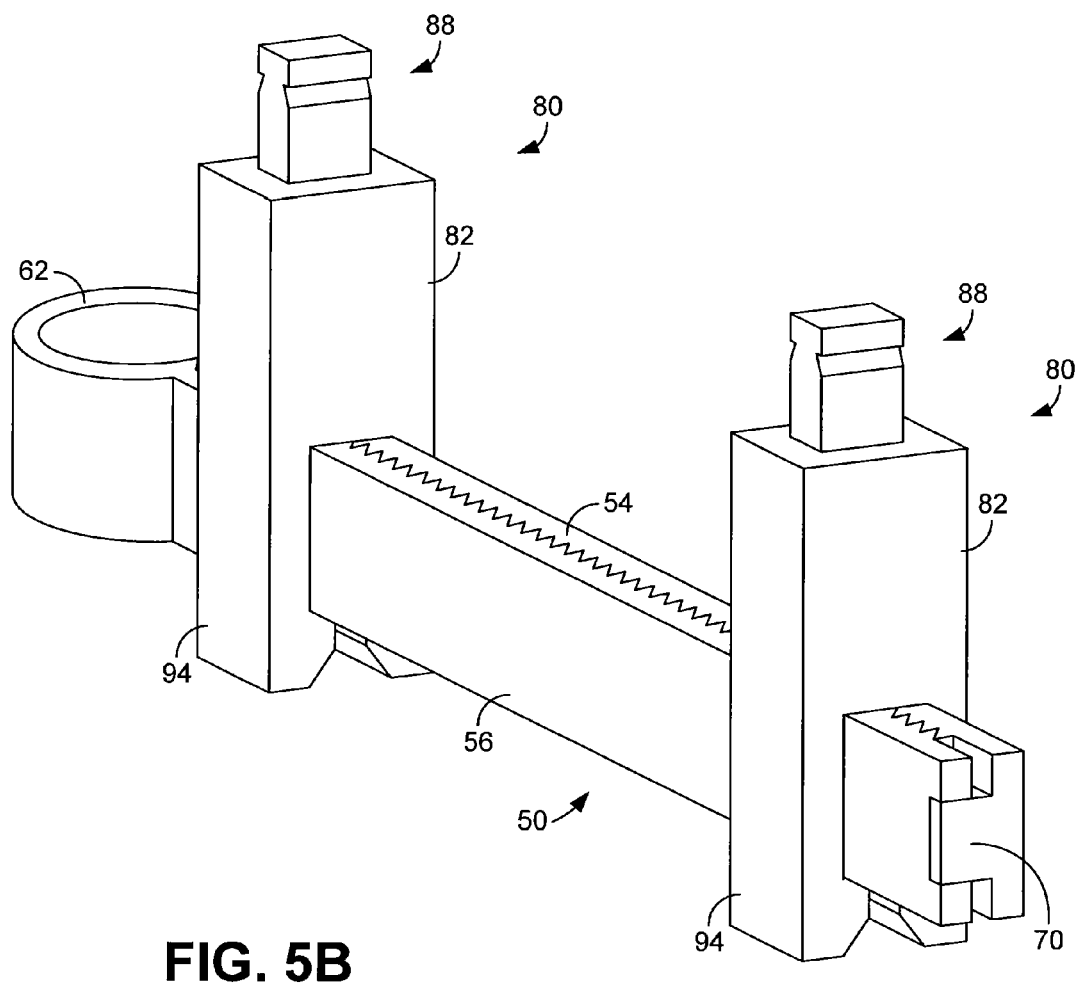

The prongs 98 form a narrow passage 97 through which an umbilicus clamp can be passed When an umbilicus is to be supported, one or more securing elements 80 can be attached to the support head 22, for example by inserting the shanks 88 of the elements into the orifices provided in the head. Once the securing elements 80 are mounted to the support head 22, an umbilicus can be supported by the apparatus 10. Assuming that an umbilicus clamp 50 has already been secured to the umbilicus, the clamp can be secured by the securing elements 80. With reference to FIG. 5A, the umbilicus clamp 50 can be inserted into the "jaws" of the securing elements 80 that are formed by the opposed flexible arms 94. In particular, the closed clamp 50 can be urged upwardly between the arms 94 of the securing elements 80 and through the passages 97 to cause the arms 94 to flex outwardly and enable the clamp to pass into the openings 96 of the securing elements, as depicted in FIG. 5B. After umbilical vessel cannulation has been performed the support elements 80 can be removed from the support head 22 and discarded. It will be appreciated that differently sized and configured securing elements can be provided to secure differently sized and configured umbilical clamps. The removability of the securing elements enables interchangeability so that substantially every type of umbilicus clamp can be secured by the apparatus 10.

Figure 6:
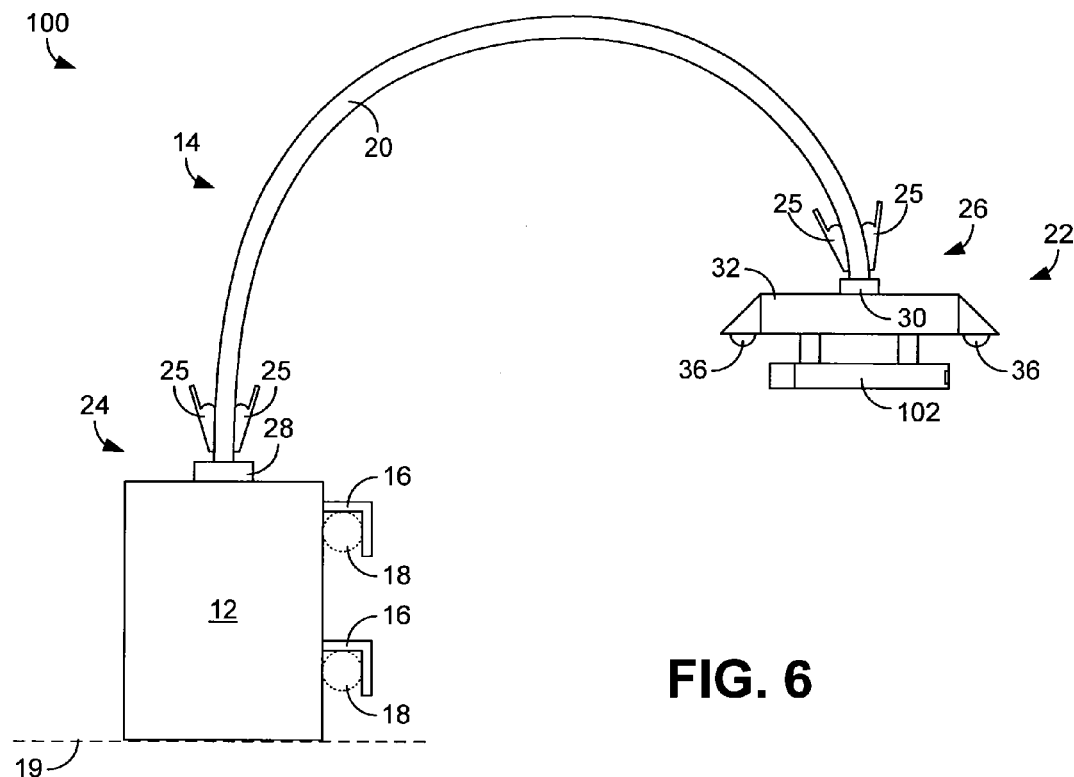
FIG. 6 is a schematic side view of a further embodiment of an umbilicus support apparatus that can assist with umbilical vessel cannulation.
Figure 7:
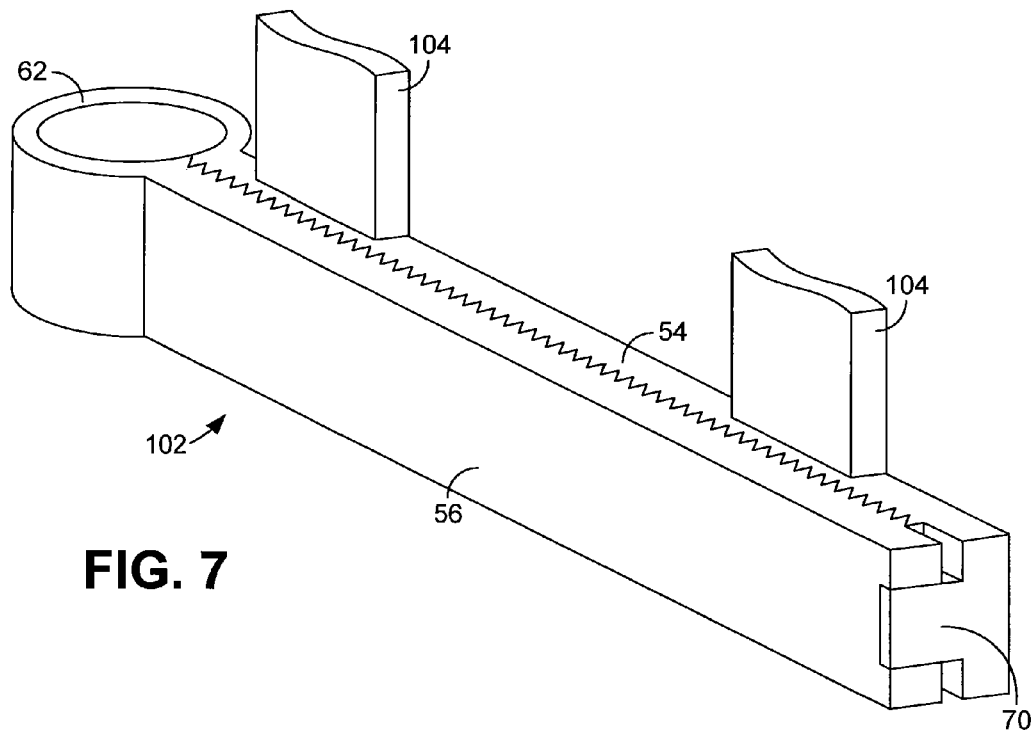
FIG. 7 is a perspective view of an umbilicus clamp that can form part of the apparatus of FIG. 6.

FIG. 6 illustrates a further embodiment of an umbilicus support apparatus 100. The apparatus 100 is similar in many ways to the apparatus 10. However, the apparatus 100 comprises an integrated umbilicus clamp 102 with integrated securing elements. As indicated in FIG. 7, the umbilicus clamp 102 is similar in design to the independent clamp 50 shown in FIG. 3. The umbilicus clamp 102, however, includes clamp securing elements with integrated shanks 104 (shown in partial view) that extend upward from the arm 54 and are adapted to be received by the support head 22. Therefore, instead of securing an umbilicus clamp to an umbilicus and then gripping the clamp with securing elements, an umbilicus can be directly secured and supported using the integrated umbilicus clamp 102. Like the securing elements 80, the clamp 102 can be unitarily formed from a polymeric material and can be disposable.

Although various embodiments have been described above, it is to be understood that alternative embodiments are possible. The present disclosure is intended to extend to all such embodiments.

We claim:

1. An umbilicus support apparatus comprising:
   a base; and
   an armature that extends from the base, the armature including a flexible arm having a proximal end and a distal end, the armature further including a support head attached to the distal end of the flexible arm, where the support head is secured to end portions of an umbilicus clamp by a plurality of clamp securing elements, where the umbilicus clamp is configured to clamp onto an umbilicus and the plurality of clamp securing elements are separated and configured to secure the end portions of the umbilicus clamp on opposite sides of the umbilicus.

2. The apparatus of claim 1, wherein the base comprises a clamp member that secures the base to a neonate bed or incubator.

3. The apparatus of claim 1, wherein the base comprises an internal power source.

4. The apparatus of claim 1, wherein the flexible arm can be rotated relative to the base.

5. The apparatus of claim 4, wherein the armature includes a lock collar that releasably locks the flexible arm in a particular angular orientation relative to the base.

6. The apparatus of claim 1, wherein the flexible arm is adapted to provide resistance to flexion such that the flexible arm automatically remains in positions or orientations in which it is placed.

7. The apparatus of claim 1, wherein the plurality of clamp securing elements comprise flexible clip elements that are configured to receive and secure the end portions of the umbilicus clamp to the support head while the umbilicus clamp is being used to clamp onto the umbilicus.

8. The apparatus of claim 1, wherein the plurality of clamp securing elements are a plurality of shanks that are integrated with the end portions of the umbilicus clamp.

9. The apparatus of claim 1, wherein the support head comprises a light adapted to illuminate the umbilicus.

10. The apparatus of claim 1, wherein the support head can be rotated relative to the flexible arm.

11. The apparatus of claim 10, wherein the armature includes a lock collar that releasably locks the support head in a particular angular orientation relative to the flexible arm.

12. The apparatus of claim 1, wherein the armature further includes a clip adapted to secure a sterile drape or sheath that covers the flexible arm.

13. A method for supporting an umbilicus, the method comprising:
    placing an umbilicus clamp on the umbilicus adjacent its distal tip;
    positioning a support head supported by a flexible arm adjacent the umbilicus; and
    securing the umbilicus clamp to the support head with a plurality of umbilicus clamp securing elements provided on the support head to support the umbilicus in a desired position and orientation.

14. A method for supporting an umbilicus, the method comprising:
    positioning a support head supported by a flexible arm adjacent the umbilicus; and
    securing an integrated umbilicus clamp of the support head to the umbilicus to support the umbilicus in a desired orientation, the integrated umbilicus clamp comprising a plurality of clamp securing elements that secure the integrated umbilicus clamp to the support head via an integrated shank.

15. An umbilicus support apparatus comprising:
    a base that secures to a bed or incubator; and
    an armature that extends from the base, the armature including:
        a flexible arm having a proximal end and a distal end, the proximal end being connected to the base, wherein the flexible arm can be rotated relative to the base;
        a first locking collar that releasably locks the flexible arm in a particular angular orientation relative to the base;
        a support head attached to the distal end of the flexible arm, wherein the support head can be rotated relative to the flexible arm, the support head secured to end portions of an umbilicus clamp by a plurality of clamp securing elements, where the umbilicus clamp is configured to clamp onto an umbilicus and the plurality of clamp securing elements are separated and configured to secure the end portions of the umbilicus clamp on opposite sides of the umbilicus; and
        a second locking collar that releasably locks the support head in a particular angular orientation relative to the flexible arm.

16. The apparatus of claim 15, wherein the flexible arm is adapted to provide resistance to flexion such that the flexible arm automatically remains in positions or orientations in which it is placed.

17. The apparatus of claim 15, wherein the plurality of clamp securing elements are configured to releasably secure the umbilicus clamp to the support head while the umbilicus clamp is being used to clamp to the umbilicus.

18. The apparatus of claim 15, wherein the plurality of clamp securing elements are a plurality of shanks that are integrated with the end portions of the umbilicus clamp.

19. The apparatus of claim 15, wherein the support head comprises a light adapted to illuminate the umbilicus.

20. The apparatus of claim 15, wherein the armature further includes a first clip provided near the proximal end of the flexible arm, the first clip adapted to secure a first end of a sterile drape or sheath that covers the flexible arm, and a second clip provided near the distal end of the flexible arm, the second clip adapted to secure a second end of the sterile drape or sheath.

* * * * *